(12) United States Patent
Rudd et al.

(10) Patent No.: US 6,816,647 B1
(45) Date of Patent: Nov. 9, 2004

(54) COMPACT FIBER PIGTAILED TERAHERTZ MODULES

(75) Inventors: James V. Rudd, Ann Arbor, MI (US); Matthew W. Warmuth, Ann Arbor, MI (US); Steven L. Williamson, Ann Arbor, MI (US); David A. Zimdars, Ann Arbor, MI (US)

(73) Assignee: Picometrix, Inc., Ann Arbor, MI (US)

( * ) Notice: Subject to any disclaimer, the term of this patent is extended or adjusted under 35 U.S.C. 154(b) by 261 days.

(21) Appl. No.: 10/110,178

(22) PCT Filed: Oct. 16, 2000

(86) PCT No.: PCT/US00/41172

§ 371 (c)(1), (2), (4) Date: Sep. 4, 2002

(87) PCT Pub. No.: WO01/38929

PCT Pub. Date: May 31, 2001

Related U.S. Application Data

(60) Provisional application No. 60/159,358, filed on Oct. 14, 1999.

(51) Int. Cl.[7] ............................. G02B 6/00; G02B 6/36
(52) U.S. Cl. ....................... 385/37; 250/208.4; 385/147
(58) Field of Search .......................... 250/208.4, 338.1, 250/495.1, 341.1; 324/629; 359/326; 385/31, 37, 39, 147

(56) References Cited

U.S. PATENT DOCUMENTS

| | | |
|---|---|---|
| 4,199,222 A | 4/1980 | Ikushima et al. |
| 4,639,075 A | 1/1987 | Salour et al. |
| 5,127,072 A | 6/1992 | Blauvelt et al. |
| 5,401,953 A * | 3/1995 | Spencer et al. .......... 250/208.4 |
| 5,623,145 A | 4/1997 | Nuss |
| 5,663,639 A | 9/1997 | Brown et al. |
| 5,710,430 A | 1/1998 | Nuss |

(List continued on next page.)

FOREIGN PATENT DOCUMENTS

| | | |
|---|---|---|
| DE | 44 15 269 A | 11/1995 |
| EP | 0 828 143 A2 | 11/1998 |
| EP | 1 202 664 A0 | 5/2002 |
| WO | WO 01/6915 | 2/2001 |

OTHER PUBLICATIONS

N. Froberg et al. "Terahertz Radiation from a Photoconducting Antenna Array" vol. 28 No. 10, Oct. 1992 *IEEE Journal of Quantum Electronics*.

R. Lai et al. "A photoconductive, miniature terahertz source" vol. 72, No. 24, Jun. 15, 1998 *American Institue of Physics*.

Y. Pastol et al. "Characterisation of an Optoelectronically Pulsed Equiangular Spiral Antenna" vol. 26, NO. 2, Jan. 1990 *Electronics Letters*.

M. Feuer et al. "100 GHz Wafer Probes Based on Photoconductive Sampling" vol. 5, No. 3 Mar. 1993 *IEEE Photonics Technology Letters*.

*Primary Examiner*—Akm Enayet Ullah
(74) *Attorney, Agent, or Firm*—Brinks Hofer Gilson & Lione

(57) ABSTRACT

An industrially hardened terahertz electromagnetic transmitter and receiver module (29) is disclosed. The electromagnetic wave module has an optic (30) which relays an optical pulse from the delivery fiber (32) to the terahertz device. The relay optic (30) allows for a greatly reduced optical spot size as compared to the output of the optical fiber. Thus, the sensitivity of the overall system is enhanced by improving the efficiency of the terahertz device. The relay optic (30) allows the small spot of light to be aligned to the electromagnetic transmitter or receiver with sub-micron precision.

49 Claims, 8 Drawing Sheets

U.S. PATENT DOCUMENTS

| | | |
|---|---|---|
| 5,729,017 A | 3/1998 | Brener et al. |
| 5,789,750 A * | 8/1998 | Nuss ........................ 250/338.1 |
| 5,894,125 A | 4/1999 | Brener et al. |
| 5,939,721 A | 8/1999 | Jacobsen et al. |
| 6,078,047 A | 6/2000 | Mittleman et al. |
| 6,388,799 B1 * | 5/2002 | Arnone et al. .............. 359/326 |
| 6,717,717 B2 * | 4/2004 | Nelson ........................ 359/326 |
| 2003/0011871 A1 * | 1/2003 | Nelson ........................ 359/326 |
| 2003/0178584 A1 * | 9/2003 | Arnone et al. ........... 250/495.1 |
| 2004/0065832 A1 * | 4/2004 | Cluff et al. ............... 250/341.1 |
| 2004/0095147 A1 * | 5/2004 | Cole ........................ 324/629 |

\* cited by examiner

COMPACT FIBER PIGTAILED TERAHERTZ MODULES

This application is a filing under 35 U.S.C. 371, which claims priority to International application Ser. No. PCT/US00/41172, filed Oct. 16, 2000, which claims the benefit of U.S. Provisional Application No. 60/159,358, filed Oct. 14, 1999.

FIELD OF THE INVENTION

The present invention relates to a terahertz transmitter or receiver module More specifically, the present invention relates to a robust modularly packaged terahertz transmitter and receiver module.

BACKGROUND OF THE INVENTION

The present invention is concerned with the generation of terahertz electromagnetic radiation by a pulsed laser in a commercially packaged system In previous applications such as in a lab environment, a laser can be pointed directly through space at an optical switching element with negligible dispersive effects. To allow the commercial use of such a system the present invention must be industrially hardened and packaged. A laser pulse in a room environment may be deflected by objects or people and will suffer degradation from atmospheric effects, unacceptable conditions in an industrial environment. The laser must also be realigned constantly due to environmental effects on the material properties of the alignment mechanisms. By incorporating optical fiber cable and rugged packaging in the present invention, the laser light is given a predetermined path of travel and allows the present invention to be precisely aligned, ruggedly seated, and bundled into compact form. A ruggedly packaged, fiber-delivered, terahertz system allows people unfamiliar with the setup, alignment, or adjustment of ultrafast lasers, semiconductor physics, and optics, to use a time-domain terahertz system for experiments and applications outside the lab environment.

Another advantage of the fiber-delivered terahertz system is the ease with which the system can be reconfigured for use in either transmission or reflection experiments. Presently, this type of reconfiguration takes days. With the system of the present invention reconfiguration takes minutes. The terahertz transceivers, in particular, need to be built using advanced telecommunication packaging techniques in order to build these units with sufficient precision and maintain their ruggedness to such that they may be used in an industrial environment By directing short (<1-ps) pulses of light to the substrate by using a fiber-delivery system, we allow for the terahertz transceivers to be freely positioned As discussed previously, present time-domain terahertz and frequency-domain terahertz systems are usable only in the research laboratory By using fiber optic packaging techniques, we are able to make these devices manufacturable and usable by people outside the research community. The basic concept compnses anchoring a fiber near the terahertz transmitter and/or receiver, giving the present invention a substantial advantage over previous free-space systems.

However, there are some drawbacks to simply butting the fiber up to the terahertz transmitter or receiver device First, the generated terahertz radiation couples into the high dielectric substrate material preferentially over air, thus improving the efficiency of the emitter if the fiber is butted up to the substrate, radiation would be coupled into the fiber, away from the emission aperture, reducing efficiency Also, the size of the beam of light emitting from the end of a single-mode fiber is about 5 $\mu$m or larger. This is too large to adequately generate or detect the terahertz radiation.

Another difficulty of present terahertz systems is the difficulty in aligning the optical axis (comprised of the optical fiber and the terahertz element) and the terahertz optics (comprised of the terahertz element and the attached hemispherical lens) The hemispherical optic is either aplanatic or collimating as disclosed in U.S. Pat. No. 5,789,750, expressly incorporated by reference herein. It should be noted that this lens can be made from any number of materials that are effective at this wavelength regime Some examples are high-resistivity silicon (>1 k$\Omega$-cm), alumina, sapphire, or even polyethylene Furthermore, this lens can be anti-reflection coated to enhance terahertz output using a number of materials including parylene.

The new and improved system of the present invention solves these and other problems found in the prior art as will be illustrated and discussed hereinafter.

SUMMARY OF THE INVENTION

The present invention provides an intermediate or relay optic (GRIN or other focusing element coupled to the optical pulse delivery fiber) that allows for an adjustable optical spot size, which enhances the sensitivity of the overall system by improving the efficiency of the terahertz transmitter and the receiver. This spot of light must be aligned to the terahertz transmitter or receiver device with sub-micron precision. By using the relay optic we obtain a lever arm on this alignment, effectively increasing the accuracy by a factor proportion to the magnification of the relay optic. That is, the lens transforms movement of the optical fiber into a smaller movement of the focused optical spot.

The alignment problem found in the prior art is solved by the present invention, for example, by using mounting plates made of a maternal similar to the lens material. The terahertz element is mounted onto a window mounting plate using alignment marks (or fiducials) that are micro-fabricated onto the plate, and the relay optic and optical fiber are mounted to an optic mounting plate. Once assembled, both subassemblies can be aligned independent of the other. By carefully designing these various elements the entire system becomes much more manufacturable and rugged than previously obtainable. The use of the mounting plates also makes it easier to environmentally seal or hermetically seal the terahertz transmitter or receiver package. The mounting plates could be made of alumina a material compatible with such a process, while the lens could be made of any other material, and with any other optical design, that would be appropriate for the application at hand.

Moreover the present invention includes the use of a fiber to deliver short optical pulses to a terahertz transmitter or receiver More specifically, the invention uses a fiber, along with an intermediate optic, to deliver a focused beam of short (<1-ps) optical pulses to a terahertz device. This device is the element containing the active area or volume in which the delivered light power either (1) interacts to produce out-going terahertz electromagnetic radiation, or (2) responds with in-coming terahertz radiation to produce an electrical signal or alter the optical beam in a measurable manner. In the first case, the device is a transmitter, and in the second, it is a receiver This terahertz device can be either a photoconductive element such as that disclosed in U.S. Pat. Nos. 5.729,017, 5,420,595 and 5,663,639 expressly incorporated by reference herein, or an electroptic or magneto-optic device such as those disclosed in U.S. Pat.

Nos. 5,952,815 or 6,111,416 expressly incorporated by reference herein.

Further objects and advantages of the present invention will become apparent by reference to the following description of the preferred embodiment and appended drawings wherein like reference numbers reflect the same feature, element or component

DETAILED DESCRIPTION OF THE PREFERRED EMBODIMENTS

Figure 1:
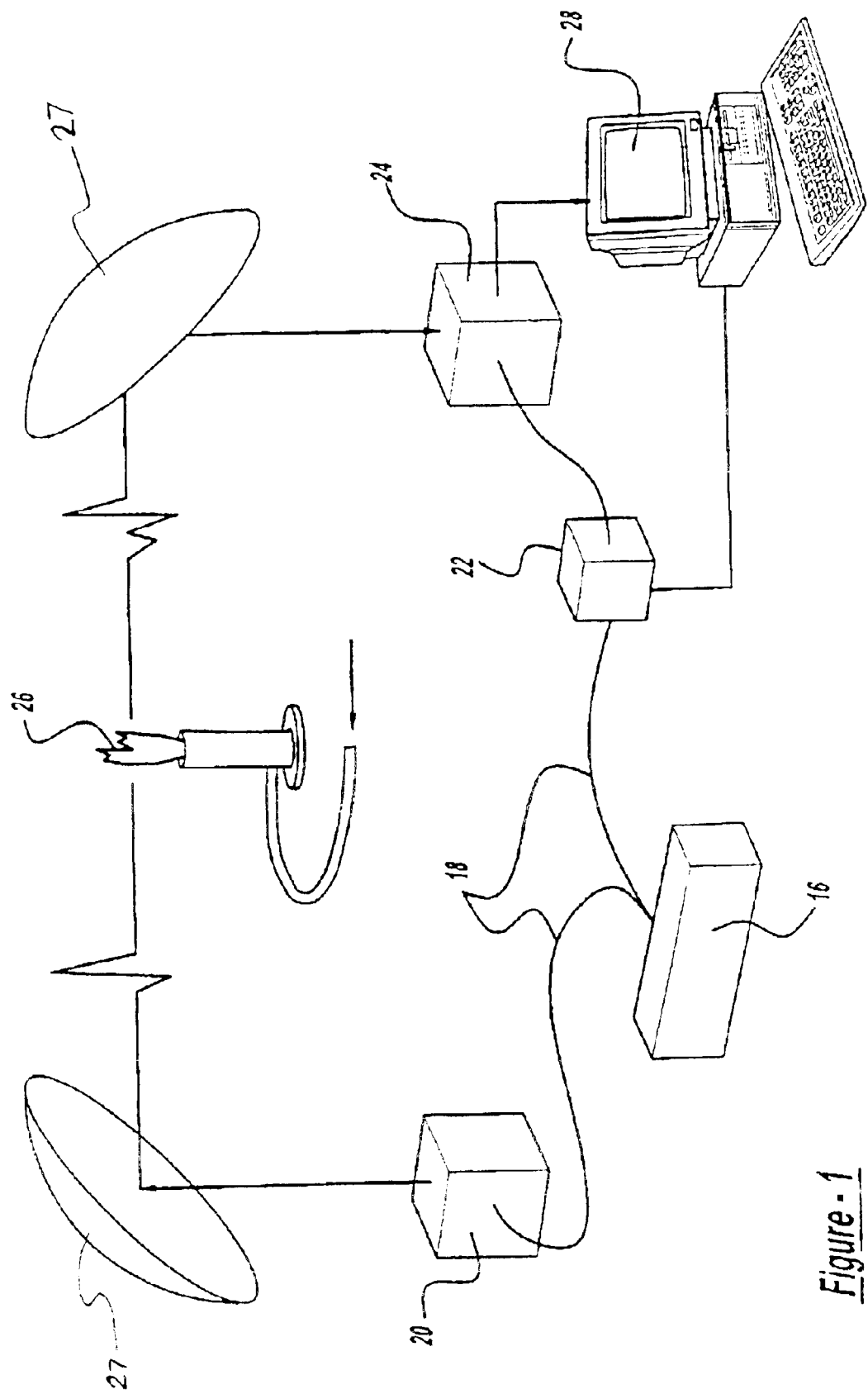
FIG. 1 is a diagrammatic overview of a terahertz electromagnetic radiation emission and detection system of the present invention.

FIG. 1 is a diagrammatic overview of one embodiment of an electromagnetic wave, such as a terahertz wave, generating and detecting system of the present invention. The system includes a pulsed Ti:sapphire laser 16 coupled by a fiber optic cable 18 to a terahertz transmitter 20, optical delay 22, terahertz optical system 27 and terahertz receiver 24. Alternatively, any pulsed laser which is capable of producing an optical pulse of less than one picosecond in duration may be substituted for the pulsed Ti:sapphire laser 16 For example, the lasers described in U.S. Pat. No. 5,880,877 and lasers such as a Ti:Sapphire laser, a Cr:LiSAF laser, a Cr:LiSGAF laser, a Cr:LiSCAF laser, an Er-doped Fiber laser, an Yb-doped fiber laser and gain switched diode laser are appropriate substitutes for pulsed sapphire laser 16. Moreover, the present invention is usable with a continuous wave source as presented in U.S. Pat. No. 5,663,639, expressly incorporated herein by reference. The terahertz transmitter 20 generates THz radiation that propagates through the first part of a terahertz optical system 27, a sample 26, a second part of a terahertz optical system 27 and is received by terahertz receiver 24 which outputs a signal proportional to the received THz radiation. The optical delay 22 determines which temporal portion of the signal is gated by the pulse at the terahertz receiver 24. The optical delay is controlled by a computer/controller 28 that further receives the output signal of the terahertz receiver 24. The terahertz optical system 27 can be of any kind described in U.S. Pat. No. 5,789,750 expressly incorporated herein by reference.

Figure 2:
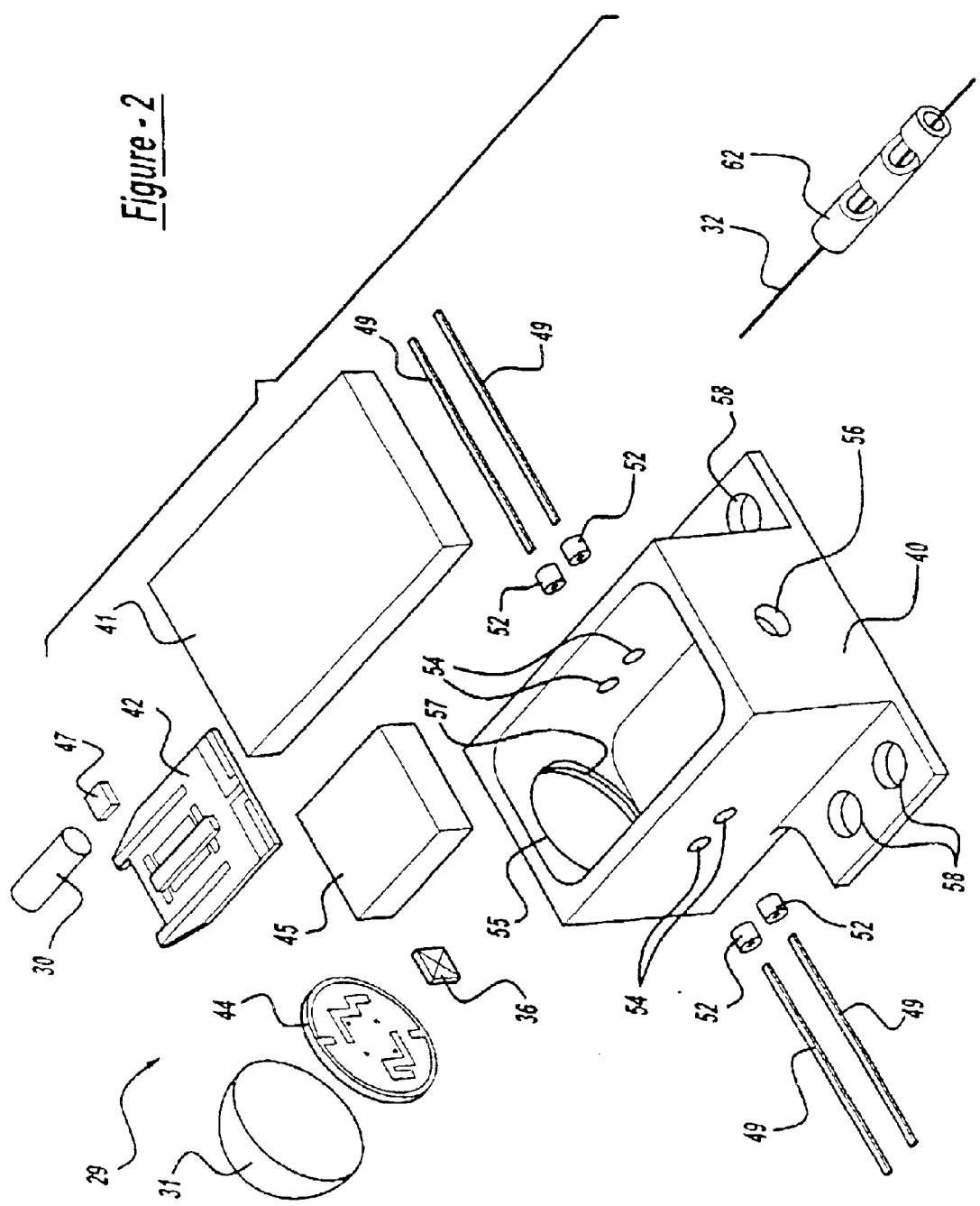
FIG. 2 is an exploded isometric view of an embodiment of the terahertz transmitter and receiver module, in accordance with the present invention.
Figure 3A:
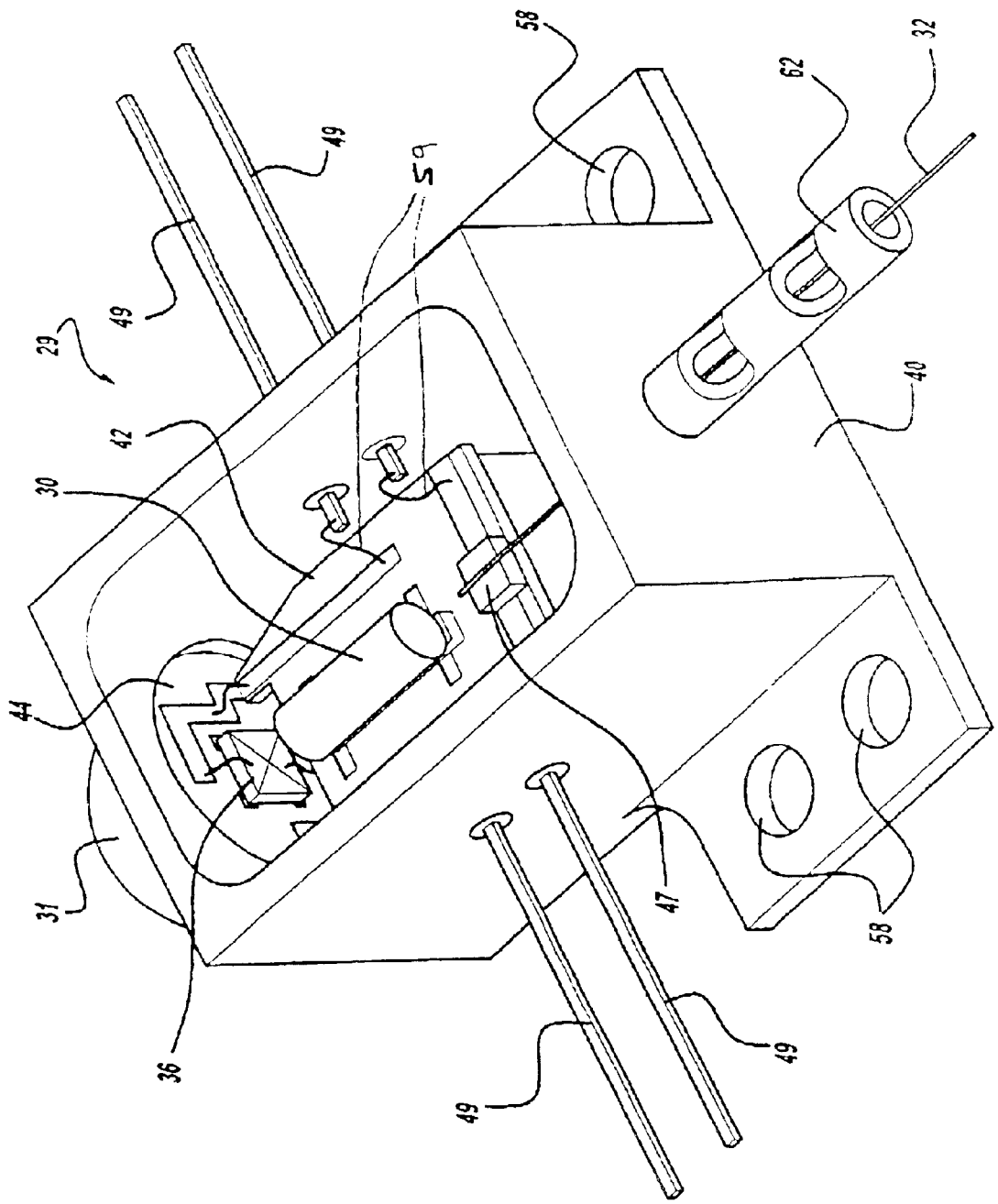
FIG. 3a is an assembled isometric view of an embodiment of the terahertz transmitter and receiver module, in accordance with the present invention.
Figure 3B:
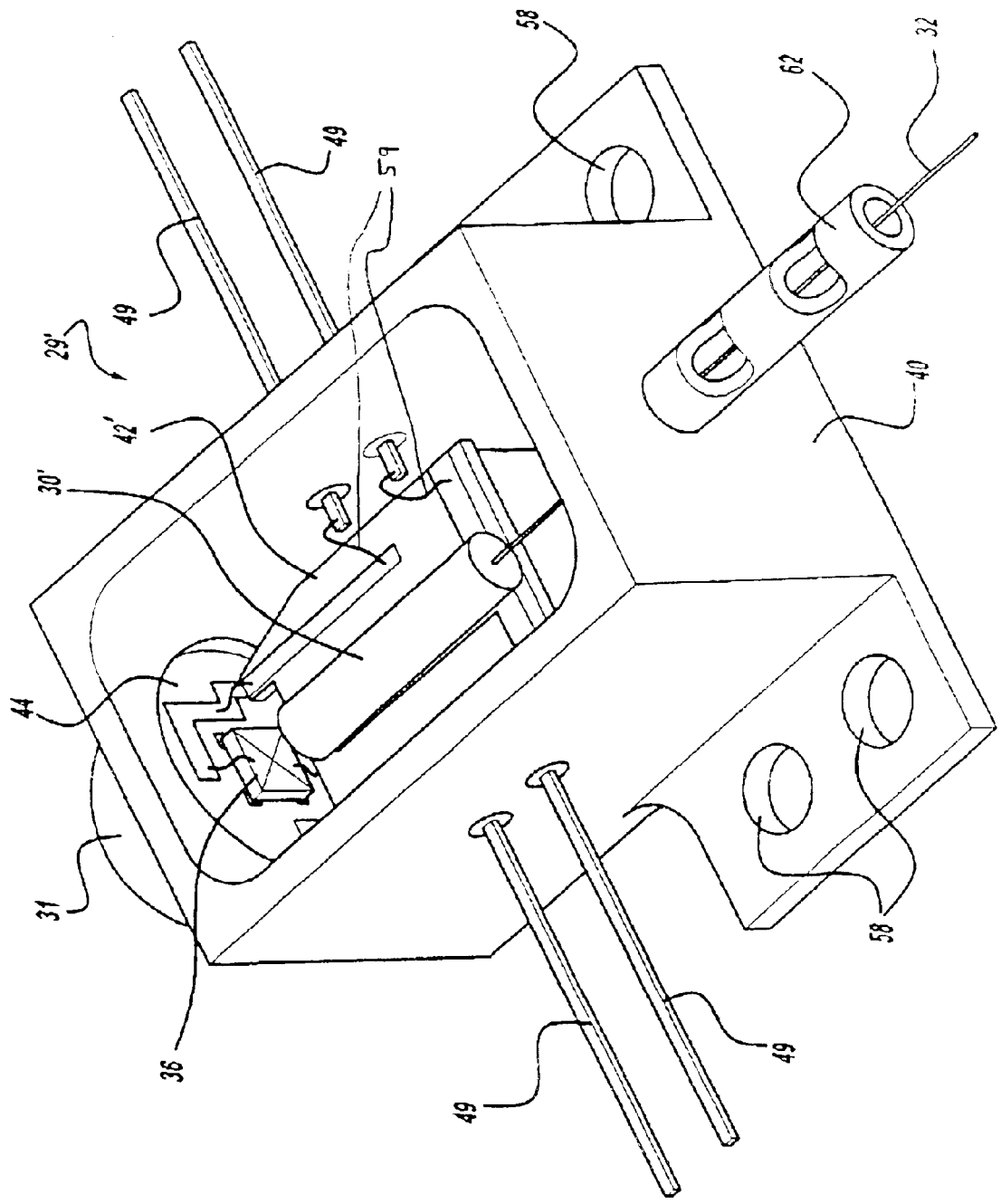
FIG. 3b is an assembled isometric view of an alternate embodiment of the terahertz transmitter and receiver module, in accordance with the present invention.
Figure 4:
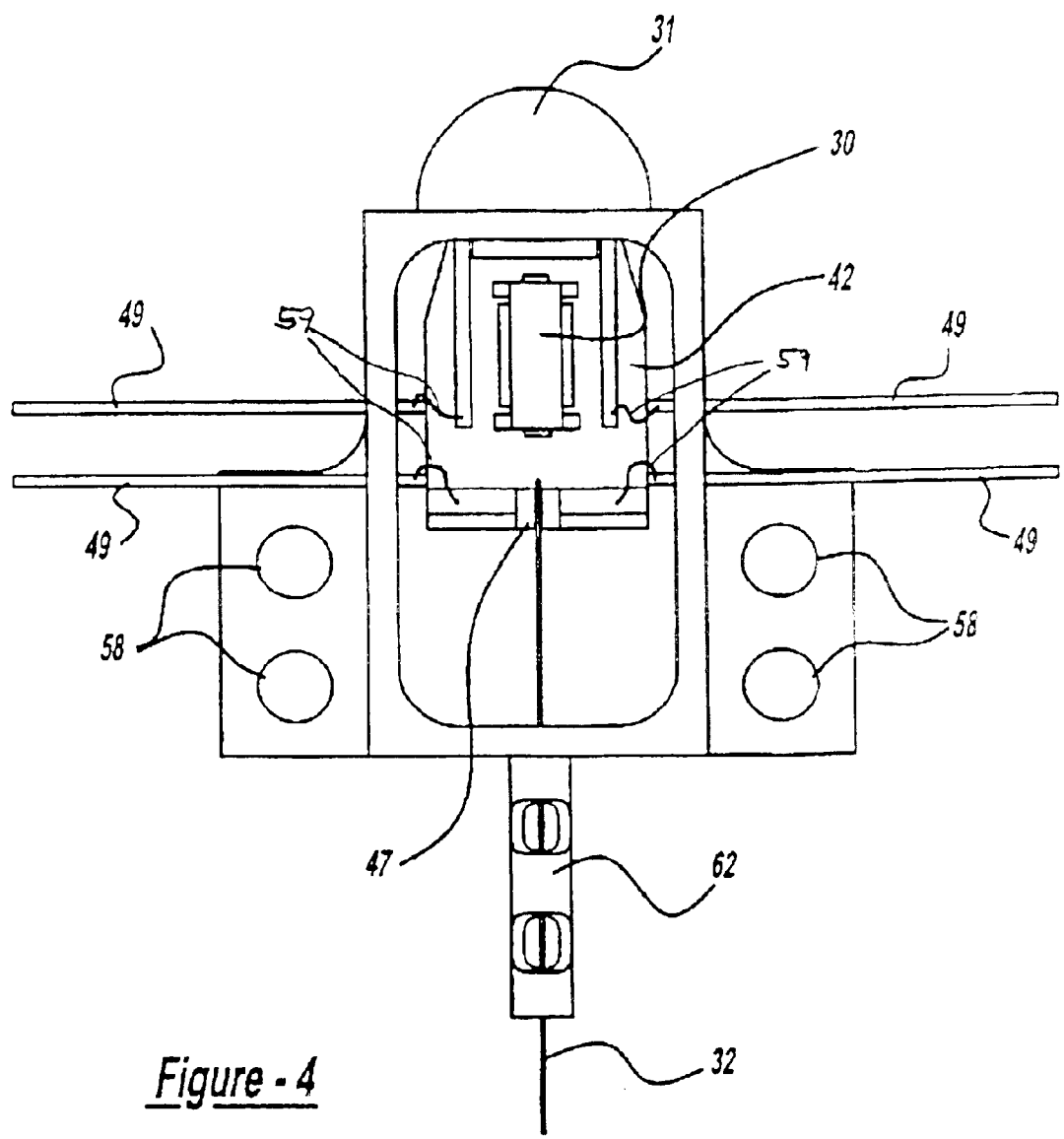
FIG. 4 is a plan view of the terahertz transmitter and receiver module, in accordance with the present invention.

FIGS. 2 through 4 illustrate embodiments of the terahertz transmitters and receivers 20 and 24 used in, for example, the system described above, in accordance with the present invention The component content and configuration of transmitters and receivers 20 and 24, as will be described hereinafter and indicated by reference numeral 29, is the same whether the device is used as an electromagnetic wave transmitter or receiver.

Figure 5:
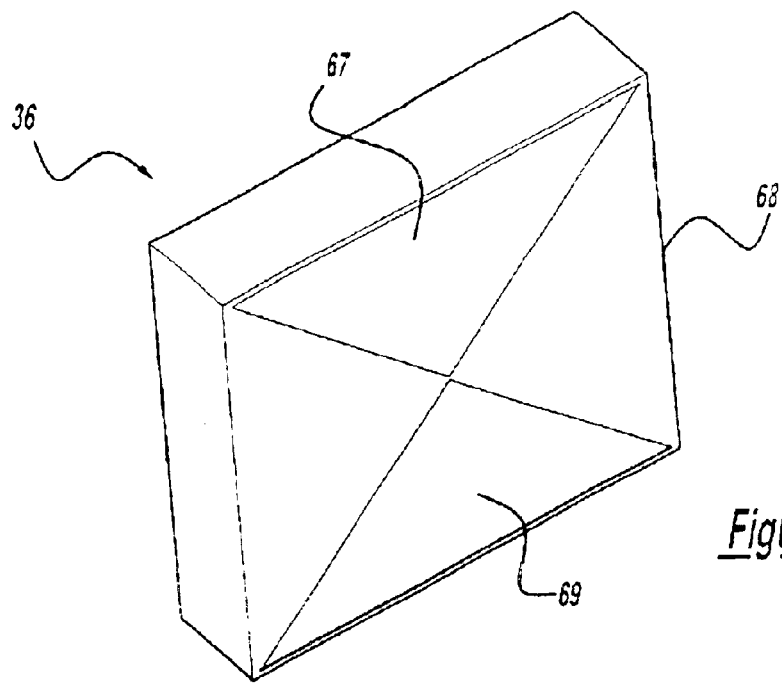
FIG. 5 is an isometric view of the photoconductive device, in accordance with the present invention.

With specific reference to FIG. 2 and FIG. 5 a terahertz device 36 is mounted within device 29 for generating or detecting the electromagnetic radiation. The terahertz device 36 has a pair of electrodes 67 and 69 bonded to a low-temperature-grown Gallium Arsenide semiconductor substrate 68 or other suitable substrate material (as shown in FIG. 5).

With continuing reference to FIG. 2, device 29 further includes a relay optic 30, such as a GRIN lens, which serves the dual purpose of making the device easier to manufacture and also helps focus the output of optical fiber 32 down to the optimal spot size. Furthermore, the relay optic 30 (or other intermediate optic) removes the fiber 32 from the immediate vicinity of the terahertz device 36, which in the case of the transmitter, could cause the emitted terahertz radiation to couple into the fiber 32 rather than into the transmitter substrate.

An industrial hardened case or module 40 having a lid 41 seals the system to protect it from environmental variables and rough handling In one embodiment of the present invention, industrial hardened module 40 contains a dry inert gas such as nitrogen. Additionally, this module can be hermetically sealed to Bellcore standards. A plurality of electrical conductor pins 49 are bonded to electrically insulating bushings 52 which are pressed into and bonded to bushing apertures 54 in housing 40. A fiber aperture 56 is is disposed in housing 40 and is configured to receive a ferrule 62 having fiber 32 bonded thereto. A plurality of mounting apertures 58 are also provided in housing 40 to mechanically secure device 29 to a mounting surface. Module body 40 may also be shaped to conform to standard parts shapes such as DIP or SOIC packages.

Further, FIG. 2 illustrates an optic mounting plate or launcher 42 that may be made from alumina or other suitable material, in accordance with the present invention. Plate 42 holds the optical relay 30, fiber pillow block 47 and fiber 32 in place as well as providing electrical contacts for the device. Plate 42 is shown in further detail in FIG. 5 for use in the preferred embodiment.

A carrier or window 44 is also provided for ease of assembly of the terahertz device to the module (as will be described below). Window 44 can be easily fabricated using standard micro-fabrication techniques. By using this window 44, which also can be silicon, or other compatible material, the assembly of device 29 is made much easier. Once this is done, the window 44 can be soldered or bonded to the module 40 A silicon, sapphire, alumina, or other style of terahertz lens 31 is mounted onto the back of window 44 for reducing the divergence of the electromagnetic wave radiation emanating from the terahertz device 36. The lens 31 configuration is generally aplanatic.

A riser block 45 and a fiber pillow block 47 are provided to position the mounting plate 42 and the fiber 32 respectively to the appropriate height above a bottom inside surface of the module to insure optical fiber alignment with the relay optic and the terahertz device The riser block of course can be integrated into the bottom floor of the module thus, reducing component piece count. The fiber pillow block 47 is bonded to the mounting plate 42 using solder or epoxy This enables the fiber 32 to be manipulated until the teraherlz signal is optimized Solder or epoxy is then deposited onto the fiber pillow block to encase the fiber. The maternal is then set to affix the fiber 32 to the pillow block 47.

FIG. 3a illustrates an embodiment of the present invention wherein fiber 32 is mounted remotely from relay optic 30.

FIG. 3b illustrates an embodiment wherein the fiber 32 is integrated with relay optic 30 creating a fiber assembly. Fiber 32 may be bonded to relay optic 30 using solder, epoxy or other appropriate bonding agent. Assemblies of this kind can also be bought commercially from many vendors. The fiber assembly is then mounted to mounting plate 42, preferably using solder. Notably, in this embodiment mounting plate 42' does not include a longitudinal slot 70 as shown in the embodiment of FIG. 3a and in greater detail in FIG. 6. Alignment of the fiber assembly is achieved by actively manipulating the entire assembly, not just the fiber as is the case in the previous embodiment.

Alternatively, the present invention contemplates integrating the relay optic 30 into the optical fiber 32. More specifically, the relay optic is formed out of the optical fiber material and configured to create a de-magnifying lens which would serve the same function as the relay optic. The lens must be configured such that an appropriate spot size is projected onto the terahertz device and wherein a minimum distance of 1/10 of the longest wavelength present is maintained between the terahertz device and the integrated lens.

FIG. 4 is a plan view of the fully assembled device 29, in accordance with the present invention Additionally, the connection of electrical jumpers 59 between mounting plate 42 and pins 49 are shown.

Figure 6:
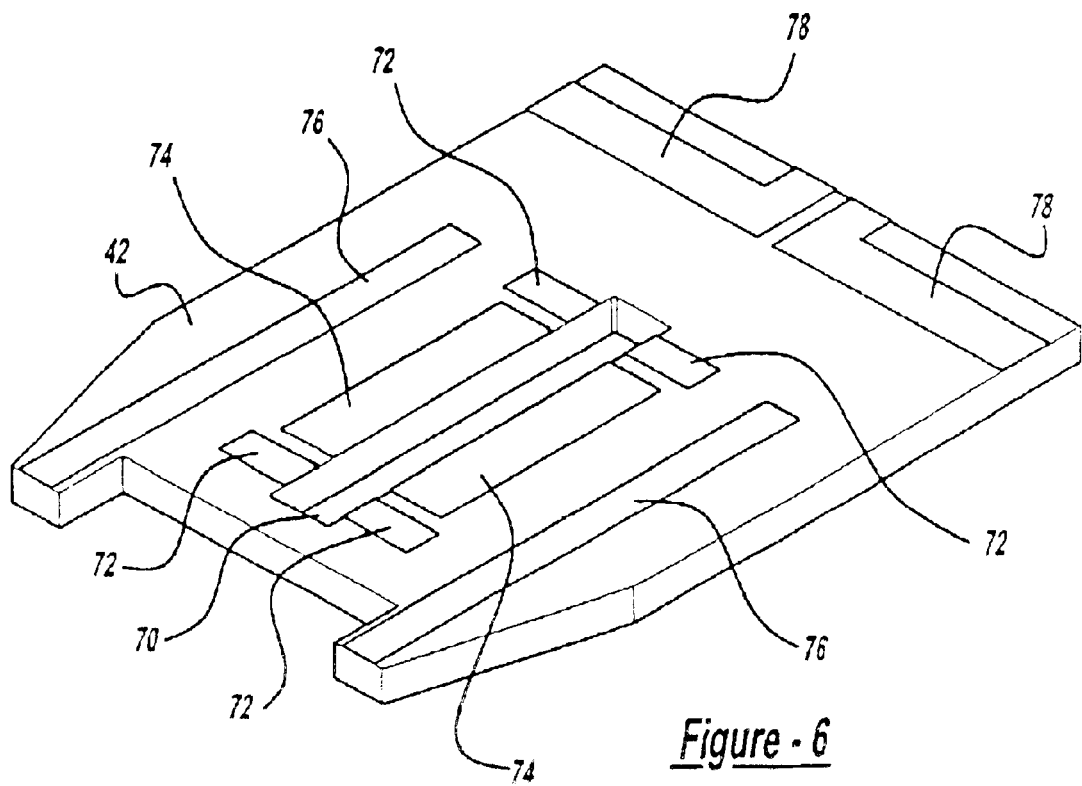
FIG. 6 illustrates the mounting plate for the relay optic and optical fiber to be used in the preferred embodiment of the present invention.

Referring now to FIG. 6 mounting plate 42 is shown in greater detail, in accordance with the present invention. Mounting plate 42 includes a longitudinal slot 70 for orienting relay optic 30 properly thereon. A plurality of fiducials 72 bonded to mounting plate 42 aid in positioning relay optic 30 longitudinally along mounting plate 42. Solder pads 74 provide a surface to bond or solder relay optic 30 to mounting plate 42. A first pair of electrically conductive traces 76 is also provided to carry electrical energy between the terahertz device 36 and pins 49. A second pair of electrically conductive traces 78 is provided to locate and attach fiber pillow block 47. Additionally, these traces may also carry current to resistively heat the solder or epoxy on the top of fiber pillow block 47 for securing the fiber 32.

Figure 7A:
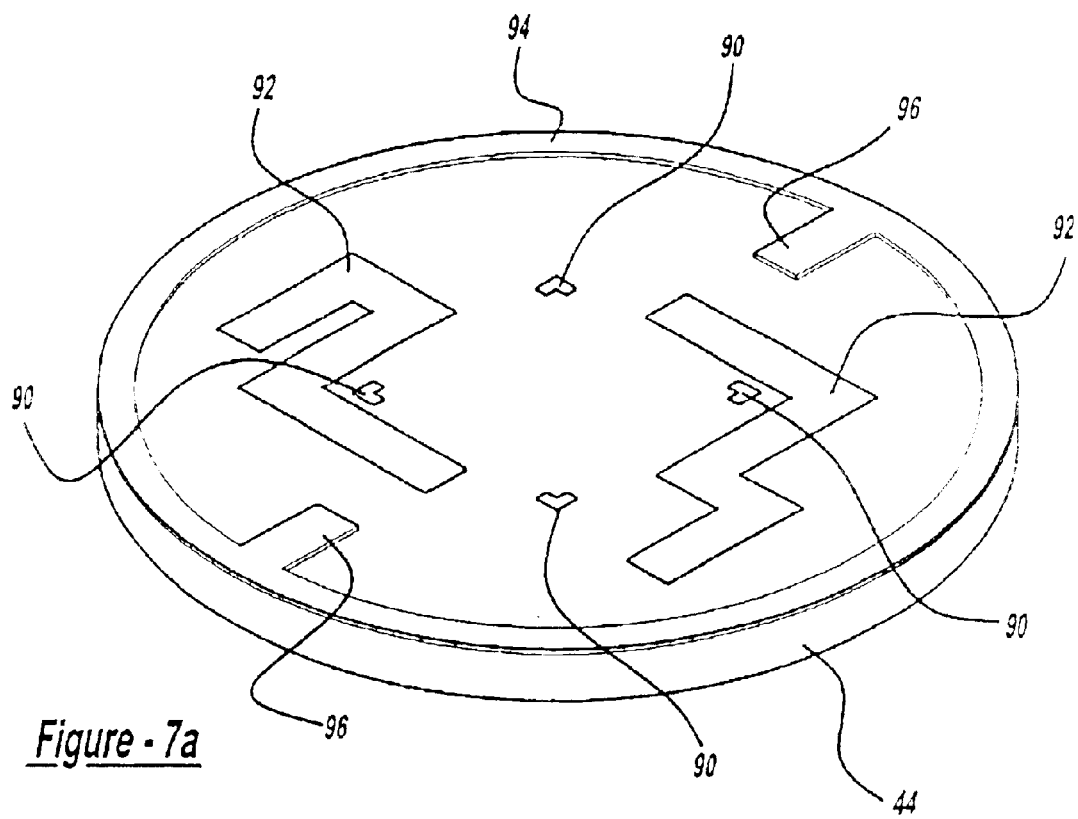
FIG. 7a is a perspective view of the mounting plate for carrying the photoconductive device to be used in the preferred embodiment of the present invention.

FIG. 7a shows the terahertz device carrier or window 44 in further detail, in accordance with the present invention. Window 44 has a set of four fiducials 90 that are provided to aid in positioning the terahertz device on window 44. Conductive traces 92 provide a path to conduct electrical energy between the antenna and pins 49 via electrical jumpers (as shown in FIG. 6b). Conductive traces 92 also act as fiducials to position mounting plate 42 adjacent window 44. Further, a perimeter trace 94 enables window 44 to be soldered to a window aperture 55 on module 40 A pair of tabs 96 are disposed on widow 44 to aid in rotationally aligning window 44 on module 40 (shown in FIG. 2).

Figure 7B:
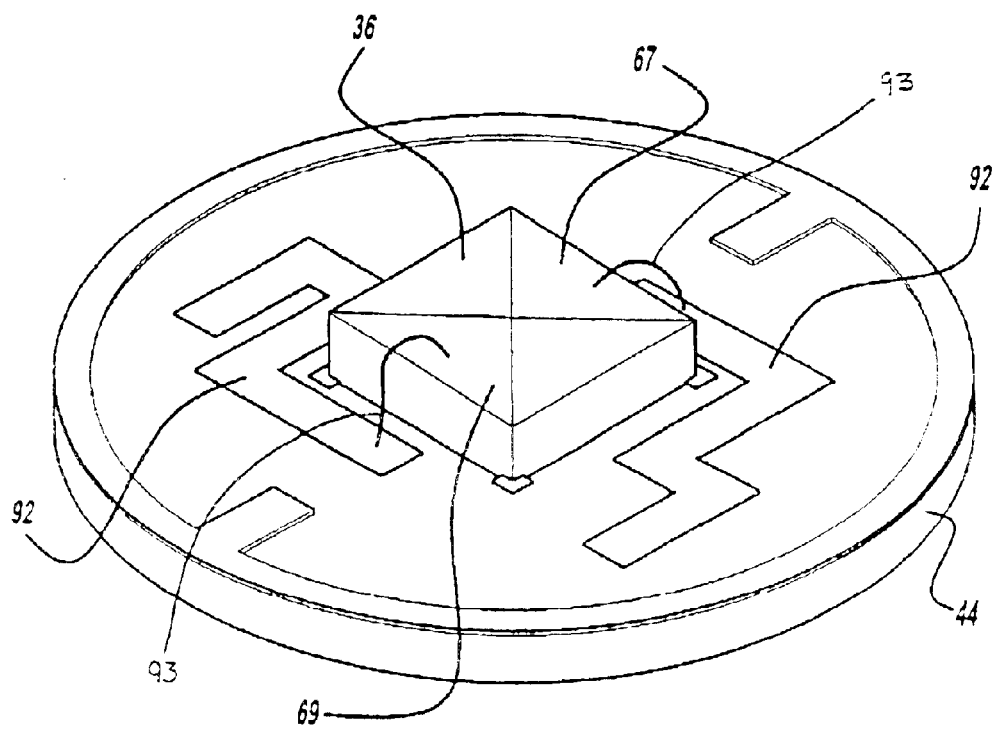
FIG. 7b is a perspective view of the photoconductive device assembled to the mounting plate to be used in the preferred embodiment of the present invention.

With specific reference to FIG. 7b photoconductive device 36 is shown assembled to window 44. Further, each of the biasing electrodes 67 and 69 are electrically connected to conductive traces 92 via electrical jumpers 93 to communicate electrical energy between the photoconductive device and window 44.

In a preferred embodiment of the present invention device 29 is assembled as described below. An electro-optic subassembly is formed by mounting the terahertz device 36 to the window 44. The electro-optic subassembly may then be bonded to the module as previously described. An optical subassembly is then formed by mounting the relay optic 30 and fiber pillow block 47 to optic mounting plate 42. Next, the riser block 45 is mounted to the bottom surface of the module 40. The optical subassembly is then positioned adjacent window 44 and bonded to the riser block Lens 31 is then bonded to window 44. The optical fiber 32 and ferrule 62 assembly is threaded through aperture 56. By actively monitoring the terahertz radiation either emitted or detected by the device, the fiber 32 can then be aligned accurately to the terahertz device and then soldered or glued into place. Then the fiber is bonded to the ferrule for strain relief and to seal the module/fiber connection. Finally, lid 41 is welded to module 40 to create a hermetically sealed package.

Figure 8:
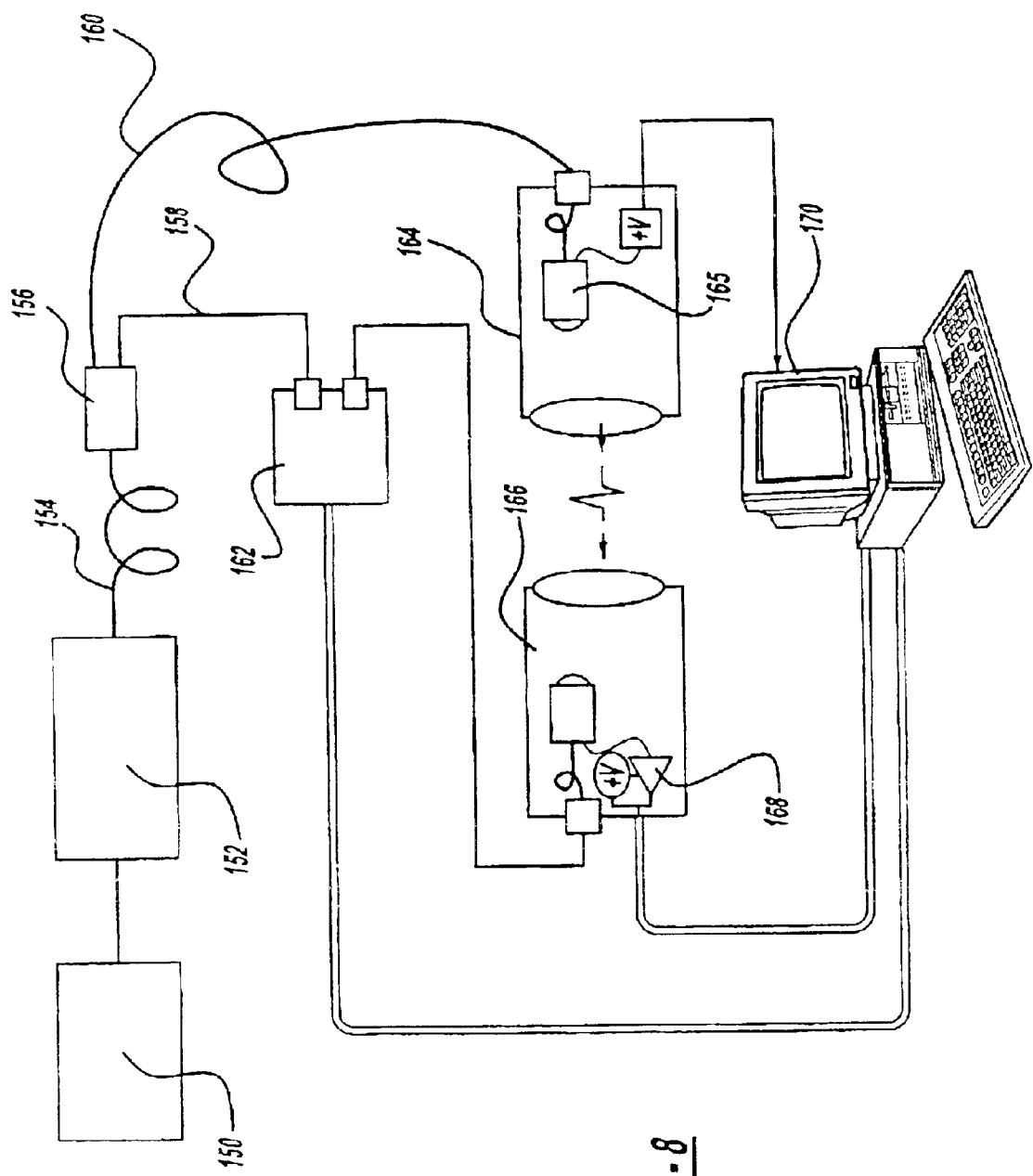
FIG. 8 is a diagrammatic overview of an alternate embodiment of the terahertz electromagnetic radiation emission and detection system of the present invention.

FIG. 8 is a diagrammatic overview of another embodiment of the terahertz electromagnetic radiation emission and detection system of the present invention. An optical pulse source 150 generates a sub-picosecond laser pulse that is dispersed in a dispersion compensator 152. The dispersion compensator can include any dispersion device such as disclosed in U.S. patent application No. 09/257,421, expressly incorporated by reference herein. The dispersed laser pulse travels through a fiber optic cable 154, fiber splitter 156, and delivery fibers 158 and 160 where it is dispersed opposite to that of the dispersion compensator. The dispersion compensator has an opposite canceling dispersion effect as compared with the entire length of optical fiber. The resultant compressed pulse traveling through delivery fiber 160, is delivered to the THz transmitter device 164 and THz radiation is generated. The pulse also travels through an optical delay 162 en route to a THz receiving device 166 The resultant compressed optical pulse contacts the THz receiver and THz radiation is detected. The resultant output signal is amplified by amplifier 168 and output to a controller/computer 170. This system conveys the light pulses used to generate the THz signal through fiber optic cables and packaged lens systems, making it rugged and substantially immune to exterior environmental conditions.

The modular packaging of a terahertz transmitter or receiver of the kind discussed in this application has never been done. Research labs have been limited to free-space optical beam coupled terahertz devices. This packaged, fiber-pigtailed module has produced the most rugged and manufacturable terahertz devices ever.

In as much as the foregoing disclosure is intended to enable one skilled in the pertinent art to practice the instant invention, it should not be construed to be limited thereby but should be construed to include such aforementioned obvious variations and be limited only by the spirit and scope of the following claims.

We claim:

1. A device for generating or detecting pulsed radiation in a frequency range of 10 GHz to 100 THz comprising an optical fiber for delivering a light wave to the device, a relay optic adjacent the optical fiber for de-magnifying the light wave projected by the optical fiber, a terahertz device disposed adjacent the relay optic for receiving the de-magnified light wave and processing or producing the radiation in the frequency range of 10 GHz to 100 THz; and a housing for stabilizing the optical fiber and the terahertz device.

2. The device of claim 1 wherein the housing is defined by a bottom surface, a top surface, and a perimeter wall surface.

3. The device of claim 1 further comprising a means for aligning the terahertz device, the optic and the optical fiber along a longitudinal alignment axis to produce a maximum energy output from the terahertz device.

4. The device of claim 1 wherein the means for aligning the terahertz device, the optic and the fiber includes by first fixing the terahertz device and the optic and then moving the fiber relative to the optic until maximum energy output of the terahertz device is achieved.

5. The device of claim 4 wherein the fiber is aligned with the optic and the terahertz device by first fixing the fiber to a mounting block and moving the mounting block relative to the housing and the relay optic until maximum energy output from the terahertz device is achieved.

6. The device of claim 1 wherein the optical fiber is bonded to the relay optic for ease of assembly and alignment.

7. The device of claim 1 wherein the optic is a GRIN lens.

8. The device of claim 1 wherein the terahertz device includes a GaAs semiconductor.

9. The device of claim 1 wherein the terahertz device includes a pair of biasing electrodes.

10. The device of claim 1 further comprising a window bonded to the housing for positioning the terahertz device adjacent the relay optic.

11. The device of claim 10 wherein the window includes at least one fiducial for positioning the terahertz device on the window.

12. The device of claim 10 further comprising a mounting plate for carrying the optic and the fiber.

13. The device of claim 12 wherein the mounting plate includes at least one fiducial for positioning the relay optic thereon.

14. The device of claim 12 wherein the mounting plate further comprises a longitudinal slot for receiving and orienting the optic.

15. The device of claim 12 wherein the mounting plate further comprises a conductive trace for carrying electrical energy thereon.

16. The device of claim 12 wherein the window includes at least one fiducial for aligning the mounting plate relative to the window.

17. The device of claim 12 further comprising a riser block for locating the mounting plate a predefined height relative to the floor of the housing.

18. The device of claim 1 further comprising an aplanatic hyperhemisphenical lens for narrowing the radiation processed or produced by the terahertz device.

19. The device of claim 1 further comprising a fiber pillow block for locating the fiber a predefined fiber height relative to the floor of the housing.

20. The device of claim 1 further comprising a lid matable with an opening in the housing for hermetically sealing the housing.

21. A device for generating or detecting pulsed radiation in a frequency range of 10 GHz to 100 THz comprising an opto-fiber assembly having the optical fiber bonded to an optic for demagnifying the light wave carried on the optical fiber;

a terahertz device disposed adjacent the relay optic for receiving the de-magnified light wave and processing or producing the radiation in the frequency range of 10 GHz to 100 THz; and a housing for stabilizing the optical fiber and the terahertz device.

22. The device of claim 21 wherein the opto-fiber assembly includes a GRIN lens.

23. The device of claim 21 wherein the terahertz device includes a GaAs semiconductor.

24. The device of claim 21 further comprising a window bonded to the housing for positioning the terahertz device adjacent the terahertz assembly.

25. The device of claim 21 wherein the window has a bow-tie antenna configuration.

26. The device of claim 21 further comprising a hemispherical lens for polarizing the output of the terahertz device.

27. The device of claim 21 further comprising a mounting plate for carrying the optic and the fiber.

28. The device of claim 27 wherein the mounting plate further comprises a longitudinal slot for receiving and orienting the optic.

29. The device of claim 27 wherein the mounting plate further comprises at least one electrically conductive trace for carrying electrical energy.

30. The device of claim 21 further comprising a riser block for locating the mounting plate a predefined height relative to a floor of the housing.

31. The device of claim 21 further comprising a fiber pillow block for locating the fiber a predefined height relative to a floor of the housing.

32. The device of claim 21 further comprising a lid matable with an opening in the housing for hermetically sealing the housing.

33. A device for generating or detecting pulsed radiation in the frequency range of 10 GHz to 100 THz comprising.

an optical fiber for delivering a light wave to the device assembly, a housing for stabilizing the optical fiber and terahertz device;

a relay optic secured to the housing adjacent the optical fiber for de-magnifying the light wave projected by the optical fiber, a terahertz device disposed adjacent the relay optic for receiving the de-magnified light wave and processing or producing the radiation in the frequency range of 10 GHz to 100 THz, a mounting plate bonded to the housing for carrying the terahertz device and, an optic mounting plate for holding the relay optic in alignment with the optical fiber, wherein the optic mounting plate is secured to the housing and positioned adjacent the terahertz device to allow for alignment of the relay optic and optical fiber with the terahertz device.

34. The device of claim 33 wherein the housing is defined by a bottom surface a top surface, and a perimeter wall surface.

35. The device of claim 33 further comprising a means for aligning the terahertz device, the optic and the optical fiber along a longitudinal alignment axis to produce a maximum energy output from the terahertz device.

36. The device of claim 35 wherein the means for aligning the terahertz device, the optic and the fiber includes the optical fiber bonded to the a fiber pillow block and wherein the fiber pillow block is mounted to the optic mounting plate using solder.

37. The device of claim 33 wherein the optical fiber is bonded to the relay optic for ease of assembly and alignment.

38. The device of claim 33 wherein the relay optic is a GRIN lens.

39. The device of claim 33 wherein the terahertz device includes a GaAs semiconductor.

40. The device of claim 33 wherein the terahertz device includes a pair of biasing electrodes.

41. The device of claim 33 wherein the mounting plate includes at least one fiducial for aiding in positioning the terahertz device on the mounting plate.

42. The device of claim 33 wherein the optic mounting plate includes at least one fiducial for positioning the relay optic thereon.

43. The device of claim 33 wherein the optic mounting plate further comprises a longitudinal slot for receiving and orienting the relay optic.

44. The device of claim 33 wherein the mounting plate further comprises a conductive trace for carrying electrical energy thereon.

45. The device of claim 33 wherein the window includes at least one fiducial for aligning the mounting plate relative to the window.

46. The device of claim 33 further comprising a riser block for locating the mounting plate a predefined height relative to the floor of the housing.

47. The device of claim 33 further comprising an aplanatic hyperhemispherical lens for narrowing an electromagnetic wave produced by the terahertz device.

48. The device of claim 33 further comprising a fiber pillow block for locating the fiber a predefined height relative to the floor of the housing.

49. The device of claim 33 further comprising a lid matable with an opening in the housing for hermetically sealing the housing.

* * * * *

UNITED STATES PATENT AND TRADEMARK OFFICE
CERTIFICATE OF CORRECTION

PATENT NO. : 6,816,647 B1 Page 1 of 1
DATED : November 9, 2004
INVENTOR(S) : James V. Rudd et al.

It is certified that error appears in the above-identified patent and that said Letters Patent is hereby corrected as shown below:

Column 6,
Line 62, immediately after "comprising" insert -- : -- (colon).
Line 63, immediately after "to the device" delete "," (comma) and substitute -- ; -- (semicolon) in its place.
Line 65, immediately after "optical fiber" delete "," (comma) and substitute -- ; -- (semicolon) in its place.

Column 7,
Line 53, delete "hyperhemisphencal" and substitute -- hyperhemispherical -- in its place.
Line 62, after "comprising" insert -- : -- (colon).

Column 8,
Line 35, immediately after "THz comprising" delete "." (period) and substitute -- : -- (colon) in its place.
Line 37, immediately after "assembly" delete "," (comma) and substitute -- ; -- (semicolon) in its place.
Line 43, immediately after "optical fiber" delete "," (comma) and substitute -- ; -- (semicolon) in its place.
Line 47, immediately after "100 THz" delete "," (comma) and substitute -- ; -- (semicolon) in its place.
Line 49, immediately after "device and" delete "," (comma) and substitute -- ; -- (semicolon) in its place.
Line 57, immediately after "bottom surface" insert -- , -- (comma).
Line 65, after "bonded to" delete "the".

Signed and Sealed this

Twenty-fourth Day of May, 2005

JON W. DUDAS
*Director of the United States Patent and Trademark Office*